US009181164B1

(12) United States Patent
Bercot et al.

(10) Patent No.: US 9,181,164 B1
(45) Date of Patent: Nov. 10, 2015

(54) METHOD OF PREPARING Z-ALKENE-CONTAINING INSECT PHEROMONES

(71) Applicant: Suterra, LLC, Los Angeles, CA (US)

(72) Inventors: Eric A. Bercot, Bend, OR (US); Brian M. Stoltz, San Marino, CA (US)

(73) Assignee: SUTERRA, LLC, Los Angeles, CA (US)

( * ) Notice: Subject to any disclaimer, the term of this patent is extended or adjusted under 35 U.S.C. 154(b) by 0 days.

(21) Appl. No.: 14/290,855

(22) Filed: May 29, 2014

(51) Int. Cl.
*C07C 45/42* (2006.01)
*C07C 47/21* (2006.01)
*C07C 45/00* (2006.01)
*C07C 41/54* (2006.01)

(52) U.S. Cl.
CPC ................. *C07C 47/21* (2013.01); *C07C 41/54* (2013.01); *C07C 45/00* (2013.01)

(58) Field of Classification Search
CPC .. C07C 45/42; C07C 45/515; C07C 2531/18; C07C 2531/28

USPC .......................................... 568/467, 486, 597
See application file for complete search history.

(56) References Cited

U.S. PATENT DOCUMENTS

| 4,198,533 A * | 4/1980 | Carney et al. .................. 568/840 |
| 4,228,093 A * | 10/1980 | Carney et al. .................. 556/482 |
| 8,115,035 B2 * | 2/2012 | Thompson et al. ........... 568/486 |

OTHER PUBLICATIONS

Whittaker et al. Monophasic Catalytic System for the Selective Semireduction of Alkynes. Organic Letters, vol. 15 (5), 1112-1115 (2013).*

* cited by examiner

*Primary Examiner* — Sikarl Witherspoon
(74) *Attorney, Agent, or Firm* — Cotman IP Law Group, PLC

(57) ABSTRACT

Insect pheromones and pheromone precursors, containing one or more Z-alkenyl groups, are prepared by treating an alkyne with a copper complex, reducing agent, and proton donor in an organic solvent. The pheromones and pheromone precursors are prepared with high stereoselectivity and substantially no over reduction.

50 Claims, No Drawings

METHOD OF PREPARING Z-ALKENE-CONTAINING INSECT PHEROMONES

BACKGROUND OF THE INVENTION

1. Field of the Invention

The invention relates to insect pheromones and their synthesis, particularly methods of synthesizing Z-alkenyl insect pheromones.

2. Description of the Related Art

Insects use sex pheromones as a form of chemical communication to attract members of the opposite sex in order to engage in reproduction. Increasingly, synthetic insect sex pheromones are used as eco-friendly alternatives to conventional pesticides. They have been used in attract-and-kill, mating disruption, mass trapping, and insect monitoring approaches to pest control, and offer a number of advantages over conventional pesticides: they only affect the targeted species, they are typically not environmentally persistent, and the target insect does not develop resistance to the treatment.

The sex pheromones produced by female moths (Lepidoptera) are complex mixtures of straight chain acetates, alcohols, and aldehydes, typically 10-18 carbons in length, with one-three double bonds. It has been stated that this class of pheromones, Type I, according to Ando's classification scheme (Ando T. et al., "Lepidopteran sex pheromones," *Top Curr Chem* 239: 51-96, 2004) accounts for roughly 75% of the known pheromones. Another class of pheromones, Type II (15%), comprises polyunsaturated hydrocarbons and epoxy derivatives with long, straight chains (C17-C23).

One example of a Type I insect sex pheromone is (Z,Z)-11,13-hexadecadienal (HDAL). HDAL has been identified as the primary component of the sex pheromones of the navel orangeworm (*Amyelois tranitella*)—a significant crop pest—and the meal moth (*Pyralis farinalis*)—which infests grains and other dry foodstuffs. A method of synthesizing HDAL in seven or more steps was described as early as 1980 (Sonnett, P. E. and R. R. Heath, "Stereospecific synthesis of (Z,Z)-11,13-hexadienal, a female sex pheromone of the navel orangeworm, *Amyelosis transitella*, (Lepidoptera:Pyralidae)" *Journal of Chemical Ecology*, 6,221-228, 1980). U.S. Pat. Nos. 4,198,533 and 4,228,093 describe similar seven or more reaction step methods. An improved synthesis of HDAL is described in U.S. Pat. No. 8,115,035.

A traditional route to accessing Z-alkenes is semi-hydrogenation of alkynes, using hydrogen gas and a Lindlar-type catalyst. Lindlar-type catalysts typically consists of palladium metal deposited on calcium carbonate or barium sulfate, with a "catalyst poison," such as lead acetate or lead oxide, added to deactivate some of the palladium active sites. Homogeneous catalysts can also be used. Traditional semi-hydrogenation has certain benefits, including low-cost reagents, reusable catalysts, high selectivity for Z isomers, clean (efficient) reactions, and a proven track record in the petroleum and fine chemicals industries. Unfortunately, the method also suffers from a number of drawbacks: Hydrogenation processes using heterogeneous catalysts can be challenging to scale; catalyst cost and availability are problematic; specialized equipment is required; the scope of viable substrates is limited; and the use of lead additives poses environmental problems.

In an effort to determine whether traditional semihydrogenation of diynes could be a viable route to (Z,Z)-1,3-dienes found in many insect pheromones, the present applicant undertook a detailed study of catalysts and conditions for the following reaction:

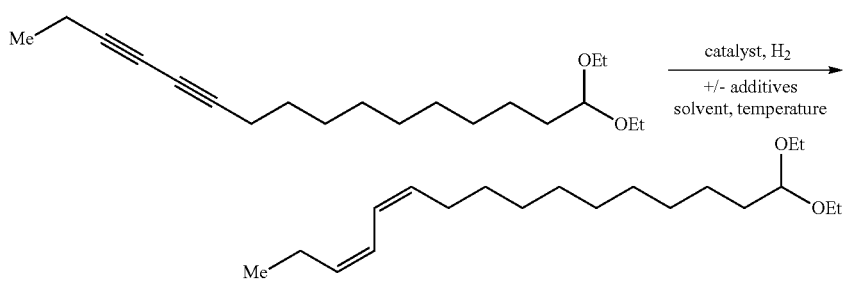

The applicant screened 22 catalysts and 22 solvents under a variety of reaction conditions, including different hydrogen pressures, different reaction times, different catalyst poisons, and several different hydrogen sources. A total of ca. 180 data points were collected over the course of more than 100 different reactions. The best result achieved was 60% conversion (alkyne to alkene), 52% desired product (the Z,Z isomer). From this, the applicant discerned that traditional semihydrogenation of alkynes is not a commercially viable route to this particular Z, Z-alkenyl insect pheromone backbone.

An alternate approach to semireduction of alkynes is described in Lalic, G., et al., "Monophasic Catalytic System for the Selective Semireduction of Alkynes," *Organic Letters*, Vol. 15, No. 5, 1112-1115, 2013. The approach uses a copper catalyst (e.g., ICyCuOtBu, IPrCuOtBu, IMesCuOtBu, etc.), a silane, and an alcohol to semi-reduce an alkyne to a Z-alkene with high stereoselectivity. The reference provides little or no guidance for the semireduction of long-chain (>C12) alkynes, mixed alkyne-alkene compounds (other than 1,3-terminal enynes), or alkynes bearing specific functional groups of interest in the manufacture of insect pheromones. Lalic et al. do not describe a method for making insect pheromones or pheromone precursors by this semireduction protocol.

SUMMARY OF THE INVENTION

The present invention provides a more efficient method of making an insect pheromone or pheromone precursor having a Z-alkenyl group, and compounds prepared by the method. In general, the method entails the steps of providing a C7-C20 alkyne having a terminal hydroxyl, protected hydroxyl, aldehyde, protected aldehyde (as the corresponding acetal), formate, ester, or halide (Cl, Br) group, and then treating the alkyne with a proton donor and a reducing agent containing at least one silicon-hydrogen bond, in the presence of a copper complex that facilitates the semireduction of an alkyne to a Z-alkene, thereby forming an insect pheromone or pheromone precursor having one or more Z-alkenyl groups, with high stereoselectivity.

DETAILED DESCRIPTION

According to a first aspect of the invention, a method is provided for making an insect pheromone or pheromone precursor by selectively semi-reducing an alkyne to a Z-alkene, the method comprising the steps of (1) providing a C7-C20 alkyne having a terminal hydroxyl, protected hydroxyl, aldehyde, protected aldehyde (as the corresponding acetal), formate, ester, or halide (Cl, Br) group; and (2) treating the C7-C20 alkyne with a proton donor in the presence of a copper(I)-nitrogen heterocyclic carbene complex ("copper (I)-NHC"), which facilitates the semireduction of the alkyne to a Z-alkene, thereby converting the C7-C20 alkyne to a C7-C20 Z-alkene having a terminal hydroxyl, protected hydroxyl, aldehyde, protected aldehyde (as the corresponding acetal), formate, ester, or halide (Cl, Br) group. Advantageously, the alkyne is converted to an insect pheromone or pheromone precursor with high stereoselectivity. In a second aspect, the invention provides C7-C20 insect pheromones or pheromone precursors having one or more Z-alkenyl groups therein, prepared by the aforementioned method.

In a preferred embodiment, the starting alkyne has any of four distinct formulas, IA-ID:

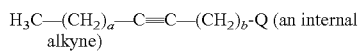 (an internal alkyne)  IA:

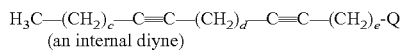 (an internal diyne)  IB:

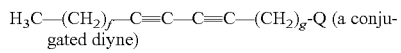 (a conjugated diyne)  IC:

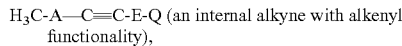 (an internal alkyne with alkenyl functionality),  ID:

where functional group Q is an aldehyde, acetate, acyclic O,O'-acetal (—CH(OR')(OR"), where R' and R" are, independently, C1 to C6 alkyl or cyclic alkyl, e.g., methyl, ethyl, propyl, butyl, cyclohexyl, etc.), cyclic O,O'-acetal (—CHO$(CH_2)_xO$— where x=2, 3, or 4), hydroxyl, protected hydroxyl, formate, ester, or halide (Cl, Br) group. Coefficients a-g are selected such that the alkyne has from 7 to 20 carbon atoms, with additional caveats:

In formula IA, a is 0 to 16, b is 1 to 7, and $4 \leq a+b \leq 17$, provided that in the case where Q is Cl or Br, then $(a,b) \neq (1,8)$. An important subclass of IA is alkynes where a is 1, 2, 3, or 4.

In formula IB, c is 0 to 13, d is 1 to 14, e is 1 to 14, and $2 \leq c+d+e \leq 15$.

In formula IC, f is 0 to 14, g is 1 to 15, and $2 \leq f+g \leq 15$.

In formula ID, groups A and E are, independently, C1 to C10 alkylenyl (e.g., —$CH_2$—, —$CH_2CH_2$—, —$CH_2CH_2CH_2$—, etc.) or alkenyl (e.g., —CH=CH—, —$CH_2$(CH=CH)—, —$CH_2CH_2$(CH=CH)—, —$CH_2$(CH=CH)$CH_2$—, etc.) groups, provided that at least one of A and E is an alkenyl group and the compound as a whole has from 7 to 20 carbon atoms.

Nonlimiting examples of protecting groups useful in the practice of the invention include tert-butyl (tBu), acetyl (Ac), silyl ($SiR_3$, where each R is, independently, phenyl or C1 to C6 alkyl or cyclic alkyl, e.g., methyl, ethyl, propyl, isopropyl, butyl, tert-butyl), pivaloyl (Piv), and acetal (tetrahydropyranyl (THP), dialkyl acetal (—$CH_2OCH(OR')(OR")$, where R' and R" are, independently, C1 to C6 alkyl or cyclic alkyl, e.g., methyl, ethyl, propyl, isopropyl, butyl, sec-butyl, tert-butyl, cyclohexyl, etc.).

The starting alkyne is selected so that the product alkene is an insect pheromone or pheromone precursor, i.e., a chemical intermediate structurally related to a desired pheromone. In some cases, the pheromone precursor differs from the actual pheromone only by the presence of a protective group]. Table 1 lists several examples of alkynes useful in the practice of the invention, the target Z-alkene products, and the pheromone-producing insect species.

TABLE 1

Representative examples of alkyne reactants, target Z-alkene products, and pheromone-producing species.

| Entry | Starting Alkyne | Product (Z)-alkene | Product description | Pheromone Producing species |
|---|---|---|---|---|
| 1 | Me–⋯–OAc | Me–⋯=⋯–OAc | pheromone component | *Eupoecilia ambiguella* |
| 2 | Me–⋯–OAc | Me–⋯=⋯–OAc | pheromone component | *Grapholita molesta* |
| 3 | Me–⋯–(  )₁,₂–OR | Me–⋯=⋯–(  )₁,₃–OR | chemical intermediate | *Platyptilia carduidactyla* and/or *Chilo suppressalis* |
| 4 | Me–⋯–OAc | Me–⋯=⋯–OAc | pheromone component | *Plodia interpunctella* |
| 5 | Me–⋯–OAc | Me–⋯=⋯–OAc | pheromone component | *Tuta absoluta* |
| 6 | Me–⋯–OR | Me–⋯=⋯–OR | chemical intermediate | *Paranthrene robiniae* |
| 7 | Me–⋯–OAc | Me–⋯=⋯–OAc | pheromone component | *Pectinophora gossypiella* |

TABLE 1-continued

Representative examples of alkyne reactants, target Z-alkene products, and pheromone-producing species.

| Entry | Starting Alkyne | Product (Z)-alkene | Product description | Pheromone Producing species |
|---|---|---|---|---|
| 8 | Me—C≡C—(CH₂)₈—CH(OEt)₂ | Me—CH=CH—(CH₂)₈—CH(OEt)₂ | chemical intermediate | *Amyelois transitella* |
| 9 | Me—CH₂—C≡C—(CH₂)₇—OAc with alkene | Me—CH₂—CH=CH—CH=CH—(CH₂)₇—OAc | pheromone component | *Lobesia botrana* |

The copper complex plays an essential role in producing a Z-alkene with high stereoselectivity and little to no over-reduction. In concert with the reducing agent and the proton donor (and, optionally, an alkoxide; see the discussion below), it facilitates Z-selective semireduction of the alkyne. Without being bound by theory, it is believed that the copper complex is either a catalyst, a catalyst precursor, or a promoter for the semireduction reaction.

In one embodiment, the copper complex is a copper(I)N-heterocyclic carbene represented by Formula II: L-Cu—X (II), where L is a nitrogen-heterocyclic carbene (NHC) and X is $OCOR^5$, $OR^5$, Cl, Br, I, or F, where $R^5$ is aryl or C1 to C5 alkyl. Presently preferred NHCs are 5-membered heterocycles containing two or three nitrogen atoms, including:
(1) imidazol-2-ylidene-based carbenes having the formula (1)

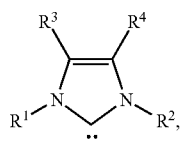

where $R^1$ and $R^2$ are, independently, alkyl (including isopropyl, tert-butyl, cyclohexyl, n-butyl, adamantyl, benzyl, and alpha-methyl benzyl) or aryl (including 2,4,6-trimethylphenyl (mesityl) and 2,6-diisopropylphenyl), and $R^3$ and $R^4$ are, independently, hydrogen, alkyl (C1 to C10), or aryl, or together $R^3$ and $R^4$ form a cycloalkenyl or aryl optionally substituted with one or more groups consisting of alkyl (C1 to C10), alkoxy (C1 to C10), and aryl;
(2) imidazolidinylidene-based carbenes having the formula (2)

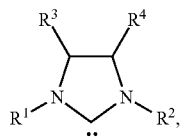

where $R^1$ and $R^2$ are, independently, alkyl (C1 to C10, including isopropyl, tert-butyl, cyclohexyl, n-butyl, adamantyl, benzyl, and alpha-methyl benzyl) or aryl (including 2,4,6-trimethylphenyl (mesityl) and 2,6-diisopropylphenyl), and $R^3$ and $R^4$ are, independently, hydrogen, alkyl (C1 to C10), or aryl, or together $R^3$ and $R^4$ form a cycloalkyl or aryl optionally substituted with one or more groups consisting of alkyl (C1 to C10), alkoxy (C1 to C10), and aryl; and
(3) 1,2,4-triazol-3-ylidene-based carbenes having the formula (3)

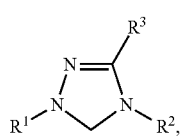

where $R^1$ and $R^2$ are, independently, alkyl (C1 to C10, including isopropyl, tert-butyl, cyclohexyl, n-butyl, adamantyl, benzyl, and alpha-methyl benzyl) or aryl (including 2,4,6-trimethylphenyl (mesityl) and 2,6-diisopropylphenyl), and $R^3$ is hydrogen, methyl or aryl, or together $R^2$ and $R^3$ form a cycloalkyl optionally substituted with one or more groups consisting of alkyl (C1 to C10), alkoxy (C1 to C10), and aryl.

NHCs and copper(I)-NHC complexes are readily prepared in a number of ways, as described in the literature. The following schemes are representative:

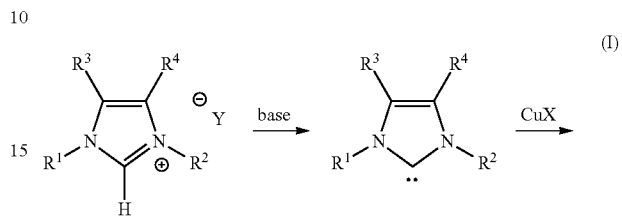

(I)

(II)

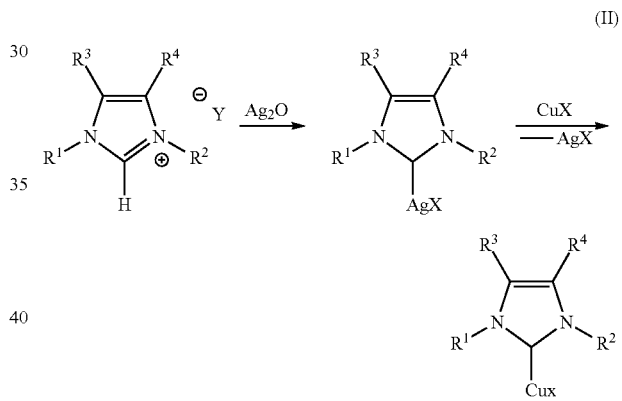

(III)

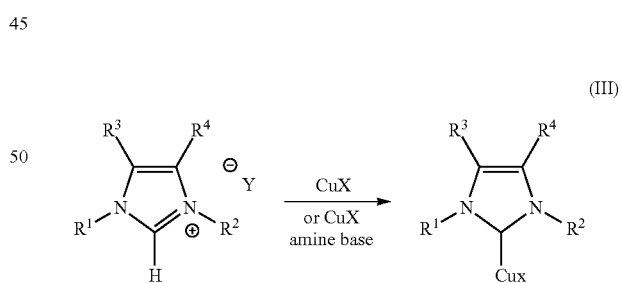

(IV)

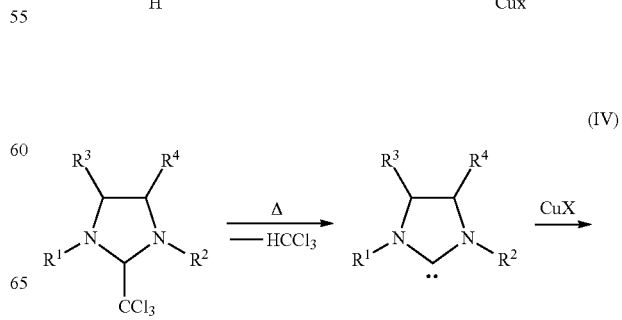

-continued

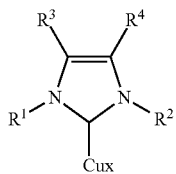

Copper(I)-NHC complexes containing an NHC other than an imidazolyidene are prepared in a similar manner, starting with the appropriate NHC. In some cases, a particular ligand X can be introduced by an exchange reaction, for example, the reaction of L-Cu—Cl with sodium tert-butoxide: L-Cu—Cl+Na$^+$[O-t-Bu]$^-$→L-Cu—O-t-Bu+NaCl.

Preferred copper(I)-NHCs are sterically hindered; the NHC ligands contain two or more bulky organic groups attached to the heterocycle, most preferably at the ring positions flanking the carbene (—C:—) carbon. Nonlimiting examples of such bulky groups include 2,6-diisopropylphenyl and 2,4,6-trimethylphenyl. A specific example of a sterically hindered copper(I)-NHC is chloro[1,3-bis(2,6-di-isopropylphenyl)imidazole-2-ylidene]copper (I) ("IPrCuCl"):

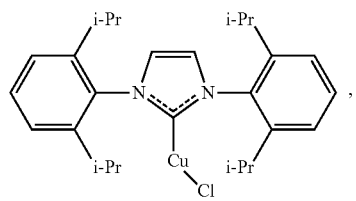

commercially available from Sigma-Aldrich (cat. No. 696307). Another sterically hindered copper(I)-NHC is the mesitylene analog, chloro[1,3-bis(2,4,6-trimethylphenyl) imidazole-2-ylidene]copper (I) ("IMesCuCl"). Closely related are the tert-butoxide analogs, IPrCuOtBu and IMesCuOtBu, and tert-amyloxide analogs, IPrCuOtAm and IMesCuOtAm, in which the chloro group has been replaced by a tertiary-butoxide or tertiary-amyloxide group. They can be prepared by treating one equivalent of IPrCuCl or IMesCuCl with one equivalent of M-OtBu or M-OtAm (where M is lithium, sodium, or potassium) in a suitable organic solvent, preferably tetrahydrofuran (THF), 2-methyl-THF, t-butanol, or t-amyl alcohol, at a temperature of from −20 to +60° C.

The preparation of IPrCuCl, IMesCuCl, and other Cu(I)-NHCs is described in Cisnetti, F., et al., "Simplified Preparation of Copper (I) NHCs using Aqueous Ammonia," *Organometallics* 2013, 32, 4279-4283, which is incorporated by reference herein in its entirety. See also Son, U. S., et al., "Cu$_2$O: A Versatile Reagent for Base-Free Direct Synthesis of NHC-Copper Complexes and Decoration of 3D-MOF with Coordinatively Unsaturated NHC-Copper Species," *Organometallics* 2010, 29, 1518-1521 (preparation of IPrCuX where X=Cl, Br, I) and Sadighi, J. P., "Synthesis, Structure, and Alkyne Reactivity of a Dimeric (Carbene)copper(I) Hydride," *Organometallics* 2004, 23, 3369-3371 (in-situ preparation of IPrCuOtBu), both references being incorporated by reference herein in their entirety.

In addition to the alkyne starting material and the copper complex, the reaction mixture includes a reducing agent containing at least one Si—H bond, and a proton donor. In the reducing agent, the silicon atom(s) is less electronegative than the adjacent hydrogen atom(s), and the "silane" serves as a radical H-donor or hydride donor. Nonlimiting examples of such compounds include trialkylsilicon hydrides, such as triethylsilane (Et$_3$SiH) and diethylmethylsilane (Et$_2$MeSiH); arylakylsilicon hydrides, such as phenyldimethylsilane (PhMe$_2$SiH); triarylsilicon hydrides, such as triphenylsilane (Ph$_3$SiH); arylchloro- and alkylarylchlorosilicon hydrides, such as methylphenylchlorosilane (PhMeClSiH) and diphenylchlorosilane (Ph$_2$SiHCl); trialkoxy- and trisiloxysilicon hydrides, such as triethoxysilane ((EtO)$_3$SiH) and tris(trimethylsiloxy)silane ((TMSO)$_3$SiH); and related oligomers and polymers, such as polymethylhydrosiloxane (PMHS).

The proton donor is typically an alcohol or other compound capable of donating a hydrogen group (H) to the reaction. Nonlimiting examples include methanol, ethanol, isopropanol, n-butanol, isobutanol, sec-butanol, tert-butanol, and tert-amyl alcohol. One or a combination of proton donors can be used.

In one embodiment, the reaction mixture also includes a metal alkoxide, preferably an alkali metal alkoxide, particularly an alkali metal tertiary-butoxide. Nonlimiting examples include sodium tert-butoxide, potassium tert-butoxide, sodium tert-amyloxide, and potassium tert-amyloxide. The alkoxide can react with the copper complex to form a catalytically active (or more active) species that facilitates Z-selective semireduction of the alkyne.

The method of converting a starting alkyne to a Z-alkenyl insect pheromone or pheromone precursor is carried out in a straightforward manner. In one embodiment, the reaction is run as a batch process by mixing the starting materials (alkyne, copper complex, reducing agent, proton donor, and alkoxide (if present) in a suitable solvent (e.g., an organic solvent, such as toluene) or mixture of solvents, at a temperature of from −50° C. to +100° C., more preferably +15° C. to +50° C. In a second embodiment, the process is run semi-batch. The copper complex is typically treated with one equivalent of metal alkoxide in a suitable organic solvent, preferably THF or 2-methyl-THF, at a temperature of −50° C. to +100° C., more preferably +15° C. to +50° C. The resulting catalyst solution is added to a mixture of starting alkyne, 1 to 10 equivalents of reducing agent, and 1 to 10 equivalents of proton donor, preferably an alcohol, in an organic solvent or mixture of solvents at a temperature of −50° C. to +100° C., more preferably +15° C. to +50° C. In a third embodiment, the reaction is run semi-batch. The copper complex is treated with one equivalent of metal alkoxide in a suitable organic solvent, preferably THF or 2-methyl THF, at a temperature of −50° C. to +100° C., more preferably +15° C. to +50° C. The resulting catalyst solution is added to a mixture of starting alkyne, 1 to 10 equivalents of reducing agent, in an organic solvent or mixture of solvents, at a temperature of −50° C. to +100° C., more preferably +15° C. to +50° C. To the resulting mixture are added 1 to 10 equivalents of a proton donor, preferably an alcohol.

EXAMPLES

The following are Nonlimiting examples of the invention.

Example 1

Preparation of 16,16-(diethoxy)-(Z,Z)-3,5-hexadecadiene

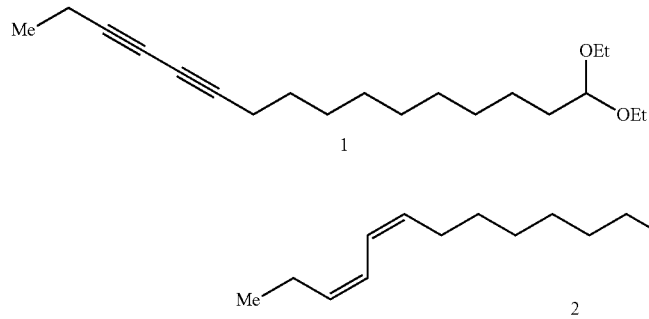

A dry 100 mL round bottom flask equipped with a magnetic stir bar intered under nitrogen was charged with chloro[1,3-bis(2,6-diisopropylphenyl)imidazol-2-ylidene]copper (I) (IPrCuCl) (1.22 g, 2.5 mmol, 0.036 equiv) and solid potassium tert-butoxide (0.300 g, 2.7 mmol, 0.039 equiv). THF (30 mL) was then added as a solvent. The resulting catalyst mixture was stirred at ambient temperature for 25 min. A second dry 500 mL round bottom flask equipped with a magnetic stir bar under a nitrogen atmosphere was charged with diyne 1 (21.3 g, 69.5 mmol, 1.0 equiv), toluene (240 mL), polymethyhydroxysilane (PMHS) (40 mL, 658 mmol, 9.5 equiv) and tert-butanol (35 mL, 366 mmol, 5.27 equiv). The catalyst solution was added to the reaction mixture via syringe. The resulting reaction mixture was stirred at ambient temperature for 18 hours. Saturated aqueous ammonium chloride (50 mL) was added to the reaction mixture and the biphasic mixture was rapidly stirred for 30 min. The phases were split and the aqueous phase back extracted with ethyl acetate (1×50 mL). The organic extracts were combined, washed with water (1×100 mL), brine (1×50 mL), dried over $Na_2SO_4$, filtered and the organic stream assayed for product content by gas chromatography. The assay indicated that the organic extracts contained 18.61 g (86% yield) of desired diene 2. The diene bears an acetal group ($—CH(OEt)_2$) at one end. It can be converted to an aldehyde by treatment with acid and water to yield the insect pheromone (Z,Z)-11,13-hexadecadienal (HDAL).

The preceding disclosure presents various aspects and embodiments of the invention, including preferred embodiments, examples, and features. From this disclosure, various modifications and alternate embodiments of the invention will be apparent to persons skilled in the art to which the invention pertains. All such modifications and embodiments are within the scope of the invention, which is limited only by the appended claims and equivalents thereof.

What is claimed is:

1. A method of making an insect pheromone or pheromone precursor, having one or more Z-alkenyl groups therein, comprising:
    treating an alkyne of formula IA, IB, IC, or ID with a copper(I)-nitrogen heterocyclic carbene complex ("copper(I)-NHC"), which facilitates semireduction of the alkyne to a Z-alkene, a reducing agent containing at least one silicon-hydrogen bond, and a proton donor, thereby forming the insect pheromone or pheromone precursor having one or more Z-alkenyl groups; wherein IA is $H_3C—(CH_2)_a—C\equiv C—(CH_2)_b-Q$, IB is $H_3C—(CH_2)_c—C\equiv C—(CH_2)_d—C\equiv C—(CH_2)_e-Q$, IC is $H_3C—(CH_2)_f—C\equiv C—C\equiv C—(CH_2)_g-Q$, and ID is $H_3C-A-C\equiv C-E-Q$;

where functional group Q is an aldehyde, acetate, acyclic O,O'-acetal (—CH(OR')(OR"), where R' and R" are, independently, C1 to C6 alkyl or cyclic alkyl), cyclic O,O'-acetal (—CHO($CH_2$)$_x$O— where x=2, 3, or 4), hydroxyl, protected hydroxyl, formate, or halide (Cl, Br) group, and coefficients a-g are selected such that the alkyne has from 7 to 20 carbon atoms; and wherein
    in formula IA, a is 0 to 16, b is 1 to 7, and 4≤a+b≤17, provided that in the case where Q is Cl or Br, (a,b)≠(1,8);
    in formula IB, c is 0 to 13, d is 1 to 14, e is 1 to 14, and 2≤c+d+e≤15;
    in formula IC, f is 0 to 14, g is 1 to 15, and 2≤f+g≤15; and
    in formula ID, groups A and E are, independently, C1 to C10 alkylenyl or alkenyl, provided that at least one of A and E is an alkenyl group and the alkyne has from 7 to 20 carbon atoms.

2. The method recited in claim 1, wherein the Copper(I)-NHC has a formula II:

$$L-Cu-X \quad (II)$$

where L is a nitrogen-heterocyclic carbene ("NHC") ligand and X is $OCOR^5$, $OR^5$, Cl, Br, I, or F, where $R^5$ is aryl or C1 to C5 alkyl.

3. The method recited in claim 2, wherein the NHC ligand is selected from the group consisting of imidazol-2-ylidenes, imidazolidinylidenes, and 1,2,4-triazolyidenes.

4. The method recited in claim 2, wherein the NHC ligand has a formula (1)

where $R^1$ and $R^2$ are, independently, alkyl or aryl, and $R^3$ and $R^4$ are, independently, hydrogen, alkyl (C1 to C10), or aryl, or together $R^3$ and $R^4$ form a cycloalkenyl or aryl optionally substituted with one or more groups consisting of alkyl (C1 to C10), alkoxy (C1 to C10), and aryl.

5. The method recited in claim 2, wherein the NHC ligand has a formula (2)

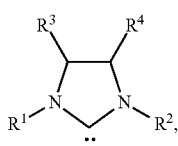

where $R^1$ and $R^2$ are, independently, alkyl (C1 to C10) or aryl, and $R^3$ and $R^4$ are, independently, hydrogen, alkyl (C1 to C10), or aryl, or together $R^3$ and $R^4$ form a cycloalkyl or aryl optionally substituted with one or more groups consisting of alkyl (C1 to C10), alkoxy (C1 to C10), and aryl.

6. The method recited in claim 2, wherein the NHC ligand has a formula (3)

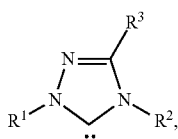

where $R^1$ and $R^2$ are, independently, alkyl (C1 to C10) or aryl, and $R^3$ is hydrogen, methyl or aryl, or together $R^2$ and $R^3$ form a cycloalkyl optionally substituted with one or more groups consisting of alkyl (C1 to C10), alkoxy (C1 to C10), and aryl.

7. The method recited in claim 1, wherein the copper(I)-NHC comprises IPrCuCl.

8. The method recited in claim 1, wherein the copper(I)-NHC comprises IMesCuCl.

9. The method recited in claim 1, wherein the copper(I)-NHC comprises IPrCuOtBu.

10. The method recited in claim 1, wherein the copper(I)-NHC comprises IMesCuOtBu.

11. The method recited in claim 1, wherein the copper(I)-NHC comprises IPrCuOtAm.

12. The method recited in claim 1, wherein the copper(I)-NHC comprises IMesCuOtAm.

13. The method recited in claim 1, wherein the insect pheromone or pheromone precursor is formed with >80% selectivity.

14. The method recited in claim 1, wherein the insect pheromone or pheromone precursor is formed with >90% selectivity.

15. The method recited in claim 1, wherein the insect pheromone or pheromone precursor is formed with >99% selectivity.

16. The method recited in claim 1, wherein the reducing agent containing at least one silicon-hydrogen bond is selected from the group consisting of $Et_3SiH$, $(EtO)_3SiH$, and polymethylhydrosiloxane.

17. The method recited in claim 1, wherein the proton donor comprises an alcohol.

18. The method recited in claim 17, wherein the alcohol is selected from the group consisting of methanol, ethanol, isopropanol, n-butanol, isobutanol, sec-butanol, tert-butanol, tert-amyl alcohol, and mixtures thereof.

19. The method recited in claim 17, wherein the alcohol comprises tert-butanol.

20. The method recited in claim 1, wherein the alkyne is selected from the group consisting of $H_3C$—$CH_2$—CC—$(CH_2)_8$—OAc, $H_3C$—$(CH_2)_2$—CC—$(CH_2)_7$—OAc, $H_3C$—$(CH_2)_{3-4}$—CC—$(CH_2)_{9-11}$—OR, $H_3C$—(CH=CH)—$(CH_2)$—CC—$(CH_2)_8$—OAc, $H_3C$—$(CH_2)$—CC—$(CH_2)$—CC—$(CH_2)_3$—(CH=CH)—$(CH_2)_2$—OAc, $H_3C$—$(CH_2)_3$—CC—$(CH_2)_8$~(CH=CH)—$(CH_2)_2$—OAc, $HC_3$—$(CH_2)_3$~(CH=CH)—$(CH_2)_2$—CC—$(CH_2)_6$—OAc, $CH_3$—$CH_2$—CC—CC—$(CH_2)_9$—CH(OEt)OEt, $CH_3$—$CH_2$—CC—(CH=CH)—$(CH_2)_6$—OAc, and mixtures thereof, where R is a protecting group.

21. The method recited in claim 1, wherein the alkyne is treated with the copper(I)-NHC, reducing agent, and proton donor in the presence of a tertiary butoxide.

22. The method recited in claim 1, wherein the step of treating the alkyne comprises forming a reaction mixture comprising the alkyne, copper complex, reducing agent, and proton donor.

23. The method recited in claim 22, wherein the reaction mixture further comprises a tertiary alkoxide.

24. The method recited in claim 22, wherein the step of treating the alkyne further comprises bringing the reaction mixture to a temperature of −50° C. to +100° C.

25. The method recited in claim 24, wherein the reaction mixture is brought to a temperature of +15° C. to +50° C.

26. A method of making an insect pheromone or pheromone precursor, having one or more Z-alkenyl groups therein, comprising:

treating an alkyne of formula IB, IC, or ID with a copper (I)-nitrogen heterocyclic carbene complex ("copper(I)-NHC"), which facilitates semireduction of the alkyne to a Z-alkene, a reducing agent containing at least one silicon-hydrogen bond, and a proton donor, thereby forming the insect pheromone or pheromone precursor having one or more Z-alkenyl groups; wherein IB is $H_3C$—$(CH_2)_c$—C≡C—$(CH_2)_d$—C≡C—$(CH_2)_e$-Q, IC is $H_3C$—$(CH_2)_f$—C≡C—C≡C—$(CH_2)_g$-Q, and ID is $H_3C$-A-C≡C-E-Q;

where functional group Q is an aldehyde, acetate, acyclic O,O'-acetal (—CH(OR')(OR''), where R' and R'' are, independently, C1 to C6 alkyl or cyclic alkyl), cyclic O,O'-acetal (—CHO$(CH_2)_x$O— where x=2, 3, or 4), hydroxyl, protected hydroxyl, formate, ester, or halide (Cl, Br) group, and coefficients a-g are selected such that the alkyne has from 7 to 20 carbon atoms; and wherein in formula IB, c is 0 to 13, d is 1 to 14, e is 1 to 14, and 2≤c+d+e≤15;

in formula IC, f is 0 to 14, g is 1 to 15, and 2≤f+g≤15; and in formula ID, groups A and E are, independently, C1 to C10 alkylenyl or alkenyl, provided that at least one of A and E is an alkenyl group and the alkyne has from 7 to 20 carbon atoms.

27. The method of claim 26, wherein the Copper(I)-NHC has a formula II:

L-Cu—X        (II)

where L is a nitrogen-heterocyclic carbene ("NHC") ligand and X is $OCOR^5$, $OR^5$, Cl, Br, I, or F, where $R^5$ is aryl or C1 to C5 alkyl.

28. The method of claim 27, wherein the NHC ligand is selected from the group consisting of imidazol-2-ylidenes, imidazolidinylidenes, and 1,2,4-triazolyidenes.

29. The method of claim 27, wherein the NHC ligand has a formula (1)

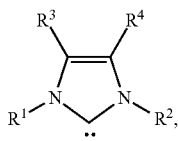

where R¹ and R² are, independently, alkyl or aryl, and R³ and R⁴ are, independently, hydrogen, alkyl (C1 to C10), or aryl, or together R³ and R⁴ form a cycloalkenyl or aryl optionally substituted with one or more groups consisting of alkyl (C1 to C10), alkoxy (C1 to C10), and aryl.

30. The method of claim 27, wherein the NHC ligand has a formula (2)

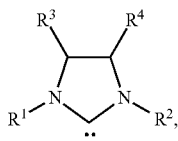

where R¹ and R² are, independently, alkyl (C1 to C10) or aryl, and R³ and R⁴ are, independently, hydrogen, alkyl (C1 to C10), or aryl, or together R³ and R⁴ form a cycloalkyl or aryl optionally substituted with one or more groups consisting of alkyl (C1 to C10), alkoxy (C1 to C10), and aryl.

31. The method recited in claim 27, wherein the NHC ligand has a formula (3)

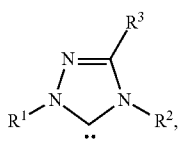

where R¹ and R² are, independently, alkyl (C1 to C10) or aryl, and R³ is hydrogen, methyl or aryl, or together R² and R³ form a cycloalkyl optionally substituted with one or more groups consisting of alkyl (C1 to C10), alkoxy (C1 to C10), and aryl.

32. The method of claim 26, wherein the copper(I)-NHC comprises IPrCuCl.

33. The method of claim 26, wherein the copper(I)-NHC comprises IMesCuCl.

34. The method of claim 26, wherein the copper(I)-NHC comprises IPrCuOtBu.

35. The method of claim 26, wherein the copper(I)-NHC comprises IMesCuOtBu.

36. The method of claim 26, wherein the copper(I)-NHC comprises IPrCuOtAm.

37. The method of claim 26, wherein the copper(I)-NHC comprises IMesCuOtAm.

38. The method of claim 26, wherein the insect pheromone or pheromone precursor is formed with >80% selectivity.

39. The method of claim 26, wherein the insect pheromone or pheromone precursor is formed with >90% selectivity.

40. The method of claim 26, wherein the insect pheromone or pheromone precursor is formed with >99% selectivity.

41. The method of claim 26, wherein the reducing agent containing at least one silicon-hydrogen bond is selected from the group consisting of $Et_3SiH$, $(EtO)_3SiH$, and polymethylhydrosiloxane.

42. The method of claim 26, wherein the proton donor comprises an alcohol.

43. The method of claim 42, wherein the alcohol is selected from the group consisting of methanol, ethanol, isopropanol, n-butanol, isobutanol, sec-butanol, tert-butanol, tert-amyl alcohol, and mixtures thereof.

44. The method of claim 42, wherein the alcohol comprises tert-butanol.

45. The method of claim 26, wherein the alkyne is selected from the group consisting of $H_3C$—$CH_2$—CC—$(CH_2)_8$—OAc, $H_3C$—$(CH_2)_2$—CC—$(CH_2)_7$—OAc, $H_3C$—$(CH_2)_{3-4}$—CC—$(CH_2)_{9-11}$—OR, $H_3C$—(CH=CH)—$(CH_2)$—CC—$(CH_2)_8$—OAc, $H_3C$—$(CH_2)$—CC—$(CH_2)$—CC—$(CH_2)_3$—(CH=CH)—$(CH_2)_2$—OAc, $H_3C$—$(CH_2)_3$—CC—$(CH_2)_8$~(CH=CH)—$(CH_2)_2$—OAc, $HC_3$—$(CH_2)_3$)~(CH=CH)—$(CH_2)_2$—CC—$(CH_2)_6$—OAc, $CH_3$—$CH_2$—CC—CC—$(CH_2)_9$—CH(OEt)OEt, $CH_3$—$CH_2$—CC—(CH=CH)—$(CH_2)_6$—OAc, and mixtures thereof, where R is a protecting group.

46. The method of claim 26, wherein the alkyne is treated with the copper(I)-NHC, reducing agent, and proton donor in the presence of a tertiary butoxide.

47. The method of claim 26, wherein the step of treating the alkyne comprises forming a reaction mixture comprising the alkyne, copper complex, reducing agent, and proton donor.

48. The method of claim 47, wherein the reaction mixture further comprises a tertiary alkoxide.

49. The method of claim 47, wherein the step of treating the alkyne further comprises bringing the reaction mixture to a temperature of −50° C. to +100° C.

50. The method of claim 49, wherein the reaction mixture is brought to a temperature of +15° C. to +50° C.

* * * * *